United States Patent
Bae et al.

(10) Patent No.: US 9,927,420 B2
(45) Date of Patent: Mar. 27, 2018

(54) METHOD OF ANALYZING SINTERED DENSITY OF URANIUM OXIDE (UOX) USING SPECTROPHOTOMETER

(71) Applicant: KEPCO NUCLEAR FUEL CO., LTD., Daejeon (KR)

(72) Inventors: Youngmoon Bae, Daejeon (KR); Seungchul Yang, Daejeon (KR); Byungkuk Lee, Sejong-si (KR); Dongyong Kwak, Daejeon (KR); Hyunkwang Cho, Daejeon (KR); Sunghoi Gu, Daejeon (KR); Euijun Hwang, Daejeon (KR)

(73) Assignee: KEPCO NUCLEAR FUEL CO., LTD., Daejeon (KR)

( * ) Notice: Subject to any disclaimer, the term of this patent is extended or adjusted under 35 U.S.C. 154(b) by 0 days.

(21) Appl. No.: 15/336,996

(22) Filed: Oct. 28, 2016

(65) Prior Publication Data
US 2018/0045703 A1   Feb. 15, 2018

(30) Foreign Application Priority Data
Aug. 9, 2016  (KR) .................. 10-2016-0101458

(51) Int. Cl.
| | | |
|---|---|---|
| *G01J 3/427* | (2006.01) | |
| *G01N 33/22* | (2006.01) | |
| *G01N 9/24* | (2006.01) | |
| *G01N 21/31* | (2006.01) | |
| *G21C 17/06* | (2006.01) | |
| *G21C 3/26* | (2006.01) | |
| *G01N 33/00* | (2006.01) | |
| *G21C 3/04* | (2006.01) | |

(52) U.S. Cl.
CPC .............. *G01N 33/222* (2013.01); *G01N 9/24* (2013.01); *G01N 21/31* (2013.01); *G21C 3/26* (2013.01); *G21C 17/06* (2013.01); *G01N 2033/0091* (2013.01); *G01N 2033/0093* (2013.01); *G21C 2003/045* (2013.01)

(58) Field of Classification Search
CPC ................. G01N 33/222; G01N 33/26; G01N 2033/0091; G01N 2033/0093; G01N 2033/045; G01N 9/24; G01N 21/31
USPC ........................................................ 356/319
See application file for complete search history.

(56) References Cited

U.S. PATENT DOCUMENTS

2013/0223582 A1*  8/2013  Rhee .................. G21C 21/02
                                                    376/419

FOREIGN PATENT DOCUMENTS

JP       2502150 B2    5/1996
KR   10-2011-0124854 A  11/2011

\* cited by examiner

*Primary Examiner* — Sunghee Y Gray
(74) *Attorney, Agent, or Firm* — Rabin & Berdo, P.C.

(57) ABSTRACT

Disclosed is a method of predicting, calculating, or analyzing the sintered density of uranium oxide ($UO_x$) before uranium oxide is added in the pelletizing process during a process of manufacturing nuclear fuel, the method including measuring the chromaticity of ammonium diuranate using a spectrophotometer. The present invention provides a simple and highly reliable method of predicting the sintered density of uranium oxide ($UO_x$), which overcomes the problem with a conventional technology where the sintered density of uranium oxide ($UO_x$) can be analyzed only in a pellet state and a subsequent treatment process needs to be performed according to the analysis result.

2 Claims, 4 Drawing Sheets

METHOD OF ANALYZING SINTERED DENSITY OF URANIUM OXIDE (UOX) USING SPECTROPHOTOMETER

CROSS REFERENCE TO RELATED APPLICATION

The present application claims priority to Korean Patent Application No. 10-2016-0101458, filed Aug. 9, 2016, the entire contents of which is incorporated herein for all purposes by this reference.

BACKGROUND OF THE INVENTION

1. Field of the Invention

The present invention relates to a method of predicting, calculating, or analyzing a sintered density of uranium oxide ($UO_x$) before the pelletizing process during a process of manufacturing nuclear fuel, the method including measuring the chromaticity of ammonium diuranate, which is a precursor of uranium oxide ($UO_x$), using a spectrophotometer.

2. Description of the Related Art

The process of manufacturing nuclear fuel includes preparing uranium oxide ($UO_x$) powder from uranium hexafluoride ($UF_6$), compacting and sintering the prepared powder to form a pellet, charging the pellet into a fuel rod, and performing assembly to manufacture a nuclear fuel assembly.

The preparation of the uranium oxide ($UO_x$) powder from uranium hexafluoride ($UF_6$) is referred to as a re-conversion process, and the re-conversion process may be classified into a dry re-conversion process and a wet re-conversion process. During the dry re-conversion process, uranium hexafluoride ($UF_6$) is reacted in a gaseous state to directly produce uranium oxide ($UO_x$) powder. The wet re-conversion process is different from the dry re-conversion process in that the uranium oxide ($UO_x$) powder is produced via ammonium diuranate or ammonium uranyl carbonate, which is a precursor, during the wet re-conversion process.

Analysis of the sintered density of uranium oxide ($UO_x$) produced using the re-conversion process is an essential technique in the process for manufacturing nuclear fuel. To date, it has not been possible to determine the sintered density of the uranium oxide ($UO_x$) powder. The sintered density is measured after the pelletizing process for manufacturing a pellet sample is finished. With regard thereto, the sintered density is calculated using the following Equation and an electrical balance measuring device.

$$\text{Sintered Density} = \frac{\text{weight}}{\text{volume}} \times \text{Correction Factor}$$

However, the above-described analysis of the sintered density has a risk factor in that since the analysis is performed to examine the quality of the pellet after the pelletizing process, a subsequent treatment process must be repeated when the sintered density is not within the range specified for nuclear fuel production. Further, the aforementioned measurement is a density measurement method that uses a volume change with the electrical balance and water, and accordingly, there are drawbacks in that pre- and post-treatment processes are very complicated and the rate of occurrence of errors depends significantly on the person performing the analysis.

In order to overcome the conventional drawbacks, the present inventors have devised a method of predicting, calculating, or analyzing the sintered density of uranium oxide ($UO_x$) before the pelletizing process, and have confirmed that the sintered density can be measured in practice, thereby accomplishing the present invention.

SUMMARY OF THE INVENTION

Accordingly, the present invention has been made keeping in mind the above problems occurring in the related art, and an object of the present invention is to provide a simple and highly reliable method of predicting and analyzing the sintered density of uranium oxide ($UO_x$) during a process of manufacturing powder for use in a uranium oxide ($UO_x$) pellets for nuclear fuel.

In order to accomplish the above object, the present invention provides a method of calculating the sintered density of a powder for use in a uranium oxide ($UO_x$) pellet for nuclear fuel during a process of manufacturing the powder for use in the uranium oxide ($UO_x$) pellet for the nuclear fuel. The method includes (1) measuring the chromaticity of an ammonium diuranate powder, which is a measurement target, using a spectrophotometer, (2) comparing the measured chromaticity data value with a standard chromaticity graph value of the ammonium diuranate powder, and (3) calculating a predicted uranium oxide ($UO_x$) sintered density of the ammonium diuranate powder, which is the measurement target, based on the comparison.

Preferably, the chromaticity data value is obtained using a L* a* b* color coordinate system.

Preferably, the chromaticity data value is obtained using an L* value of the L* a* b* color coordinate system.

According to the present invention, the problem with a conventional analysis method, in which only products produced in a pellet form can be analyzed, and the risk factor of a subsequent treatment process, which is conditionally performed depending on the analysis result, can be avoided. In addition, the chromaticity of ammonium diuranate, which is a precursor, is measured using a spectrophotometer before uranium oxide ($UO_x$) powder is manufactured to thus predict the sintered density of the uranium oxide ($UO_x$) to be manufactured, thereby reducing an average analysis time to about 20 min, which about 2.5% of the 13 hours required for the conventional method (including the pelletizing process).

Therefore, the sintered density may be analyzed and predicted during all steps of the pelletizing process using analysis data derived according to the present invention, thereby contributing to the manufacture of an optimal pellet.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
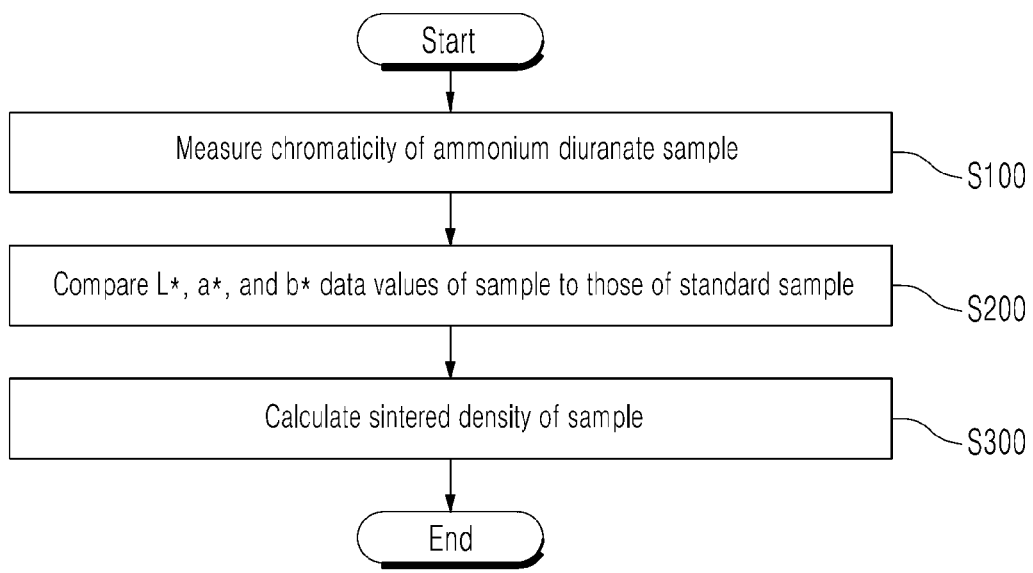
FIG. 1 is a flowchart showing the procedure of calculating the sintered density of uranium oxide ($UO_x$) powder.

Hereinafter, the present invention will be described in detail.

In order to solve the problems with the conventional method, in the present invention, the chromaticity of ammonium diuranate, generated during precipitation/filtration/drying processes of a wet re-conversion process, is measured using a spectrophotometer, thereby enabling prediction, calculation, and analysis of the sintered density of uranium oxide ($UO_x$) before the uranium oxide is added to the pelletizing process using the spectrophotometer. The method has been confirmed to have excellent predictive performance.

Spectrophotometry, as used in the present invention, is very frequently used at present in the chemical, life science, environment, and pharmaceutical fields. Such analysis is based on the measurement of an intrinsic absorption spectrum formed while various molecular motions, such as electron transition and rotation, occur by absorbing light energy depending on the type of material. Absorption spectra and energy value differences between the materials are represented using an L* a* b* color coordinate system. The spectrophotometer analysis method is extensively applied to the quantitative or qualitative analysis of organic or inorganic compounds.

Specifically, the present invention provides a method of calculating the sintered density of a powder for use in a uranium oxide ($UO_x$) pellet for nuclear fuel during a process of manufacturing the powder for use in the uranium oxide ($UO_x$) pellets for the nuclear fuel. The method includes (1) measuring the chromaticity of an ammonium diuranate powder, which is a measurement target, using a spectrophotometer, (2) comparing the measured chromaticity data value with a standard chromaticity graph value for ammonium diuranate powder, and (3) calculating a predicted uranium oxide ($UO_x$) sintered density of the ammonium diuranate powder, which is the measurement target, based on the comparison.

It is preferable for the chromaticity data value to be obtained using a L* a* b* color coordinate system.

It is preferable for the chromaticity data value to be obtained using an L* value of the L* a* b* color coordinate system.

A better understanding of the present invention may be obtained through the following Examples. It will be obvious to those skilled in the art that the Examples are set forth to illustrate the present invention but are not to be construed as limiting the scope of the present invention.

Example 1. Determination of Standard Chromaticity Graph of Ammonium Diuranate Powder First, a graph needs to be determined using standard data in order to predict, calculate, and analyze the sintered density of uranium oxide ($UO_x$) by measuring the chromaticity value of an ammonium diuranate powder sample, which is the precursor of uranium oxide ($UO_x$), using a spectrophotometer.

In the present experiment, during a precipitation process, which is an ammonium diuranate manufacturing step of a wet re-conversion process, a pH and a $NH_3$/air ratio, which are operation variables, depend on the sintered density of uranium oxide ($UO_x$). The operation variables also depended on the chromaticity of ammonium diuranate (represented using an L*a*b* color coordinate system in the present experiment).

Accordingly, ammonium diuranate powder samples are manufactured in a sufficient number while other variable factors are controlled and the predetermined operation variables are changed, and the chromaticity of each sample is measured. The samples are calcinated/reduced under the same conditions to manufacture uranium oxide ($UO_x$) powder, and then the sintered density of each sample is measured, thereby obtaining a graph based on standard data usable when the process is operated in practice. The graph may be schematized or mathematically represented for each sample that is to be subsequently measured.

Figure 2A:
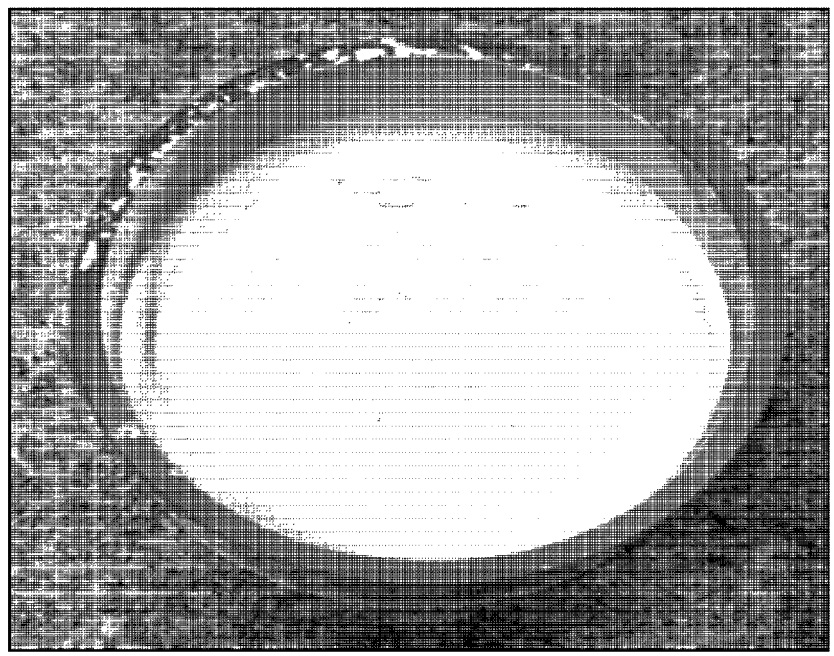
FIGS. 2A and 2B are respective pictures of ammonium diuranate powder and uranium oxide ($UO_x$) powder.
Figure 2B:
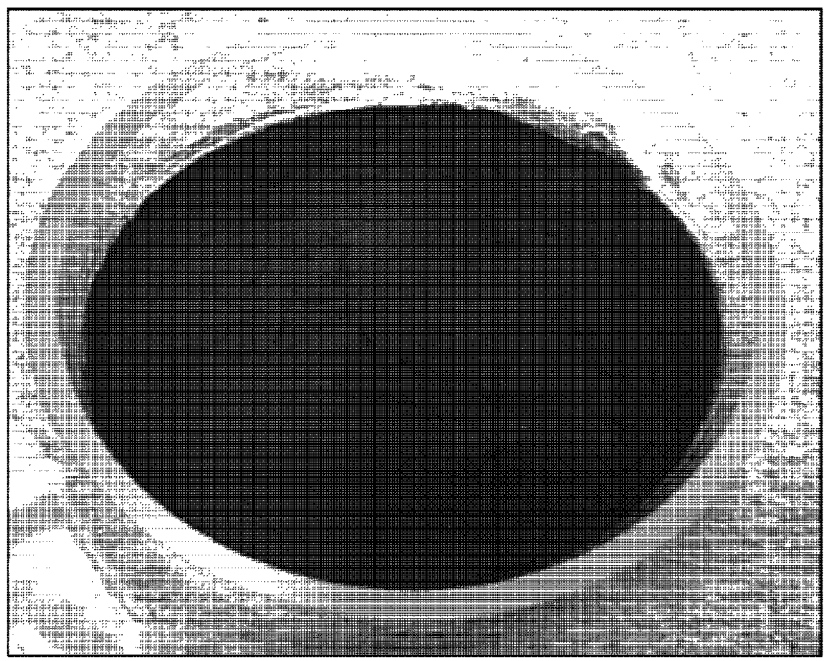

The ammonium diuranate and uranium oxide ($UO_x$) powders shown in FIGS. 2A and 2B were manufactured while the final pH and the $NH_3$/air ratio, as the operation variables of precipitation/filtration/drying, were changed. The numerical relationship between the measured chromaticity values L*, a*, and b* of ammonium diuranate and the sintered density was obtained using the graph.

Specifically, after the five ammonium diuranate samples were added in predetermined amounts to respective glass cells, calibration was performed using a spectrophotometer, followed by standard sample measurement. A trend line between the five standard samples (X axis: L*, a*, or b*, and Y axis: sintered density) was derived from L* (or a* or b*) color coordinate system data represented by the measured chromaticity values and from sintered density data of the actual pellet, thereby obtaining a standard sample formula of ammonium diuranate.

In greater detail, the values described in the following table were obtained.

| Classification | Sample characteristics | | Process of manufacturing ammonium diuranate (Within the range of operation variables) | | | | | Process of manufacturing $UO_x$ (Operation variables are fixed) | | |
| --- | --- | --- | --- | --- | --- | --- | --- | --- | --- | --- |
| | | | Operation variables [precipitation/filtration/drying] | | Ammonium diuranate | | | Operation variables [calcination/reduction] | | $UO_x$ |
| | Concentration | Solution | pH | $NH_3$/air | | | | Time/ | $N_2/H_2$/air flow | Sintered |
| | (gU/L) | (mL) | (Final) | ratio | L* | a* | b* | temperature | rate | density |
| Standard S.1 | 30 | 50 | Actual variable | Actual variable | 78.68 | 14.07 | 74.07 | Actual variable | Actual variable | 10.35 |
| Standard S.2 | " | " | Actual variable | Actual variable | 80.54 | 14.50 | 81.17 | Actual variable | Actual variable | 10.32 |

-continued

| | Sample characteristics | | Process of manufacturing ammonium diuranate (Within the range of operation variables) | | | | | | Process of manufacturing UO$_x$ (Operation variables are fixed) | | |
|---|---|---|---|---|---|---|---|---|---|---|---|
| | | | Operation variables [precipitation/ filtration/drying] | | Ammonium diuranate | | | Operation variables [calcination/reduction] | | | |
| Classification | Concentration (gU/L) | Solution (mL) | pH (Final) | NH$_3$/air ratio | L* | a* | b* | Time/ temperature | N$_2$/H$_2$/air flow rate | UO$_x$ Sintered density |
| Standard S.3 | " | " | Actual variable | Actual variable | 81.20 | 16.76 | 87.57 | Actual variable | Actual variable | 10.29 |
| Standard S.4 | " | " | Actual variable | Actual variable | 79.11 | 18.28 | 89.63 | Actual variable | Actual variable | 10.34 |
| Standard S.5 | " | " | Actual variable | Actual variable | 79.52 | 17.31 | 74.30 | Actual variable | Actual variable | 10.35 |

Figure 3:
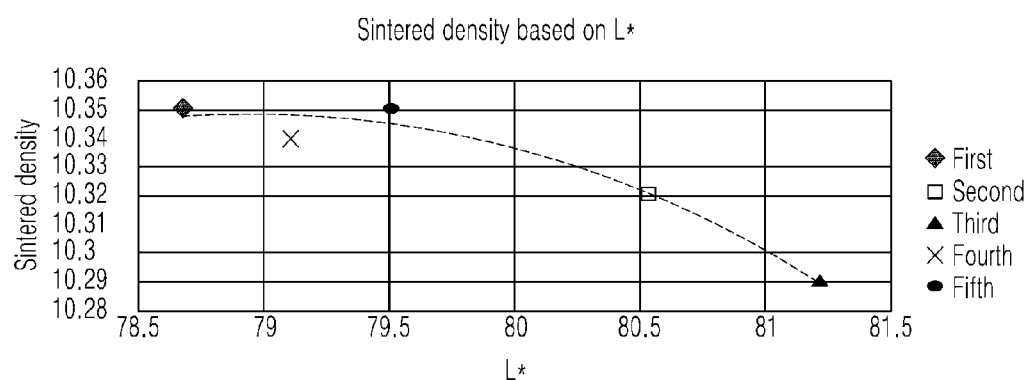
FIG. 3 is a graph showing sintered density as a function of a chromaticity value L* measured using a spectrophotometer.

From FIG. 3, it was confirmed that the relationship between the L* value and the sintered density could be represented by an Equation of a predetermined curve (represented by a quadratic function). From the R2 value of 0.9618, it was confirmed that reliability was high.

Figure 4:
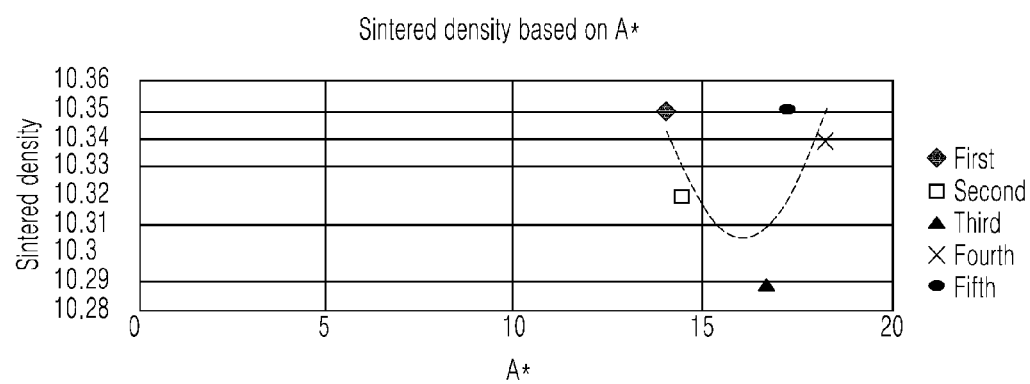
FIG. 4 is a graph showing sintered density as a function of a chromaticity value a* measured using the spectrophotometer.
Figure 5:
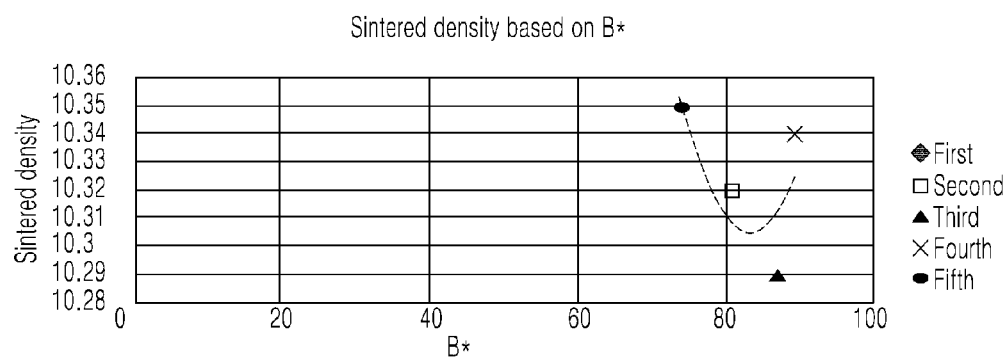
FIG. 5 is a graph showing sintered density as a function of a chromaticity value b* measured using the spectrophotometer.

On the other hand, from FIG. 4, it was confirmed that the relationship between the value a* and the sintered density could be represented by an Equation of a predetermined curve (represented by a quadratic function) but that the R2 value was 0.4034, thus exhibiting low reliability. From FIG. 5, it was confirmed that the relationship between the b* value and the sintered density could be represented by an equation corresponding to a predetermined curve (represented by a quadratic function), but that the R2 value was 0.6374, thus exhibiting low reliability.

Accordingly, it was confirmed that the sintered density could be calculated with high reliability on the basis of the L* value.

Example 2. Measurement of Chromaticity of Ammonium Diuranate Powder as Measurement Target, and Calculation of Sintered Density of Ammonium Diuranate Powder During the actual process of manufacturing powder for use in a uranium oxide (UO$_x$) pellet, the manufactured ammonium diuranate powder is sampled and added in a predetermined amount to a glass cell, and then calibration is performed using a spectrophotometer, followed by measurement. According to the aforementioned procedure, chromaticity data values are obtained using an L* a* b* color coordinate system (Step S100 of FIG. 1).

Subsequently, the data values are compared with the standard chromaticity graph values obtained in Example 1 (Step S200 of FIG. 1), and the L* value is added to the Equation to perform calculation, thereby predicting, calculating, and analyzing the sintered density value of a uranium oxide (UO$_x$) pellet that will be formed using the corresponding sample (Step S300 of FIG. 1).

Figure 6:
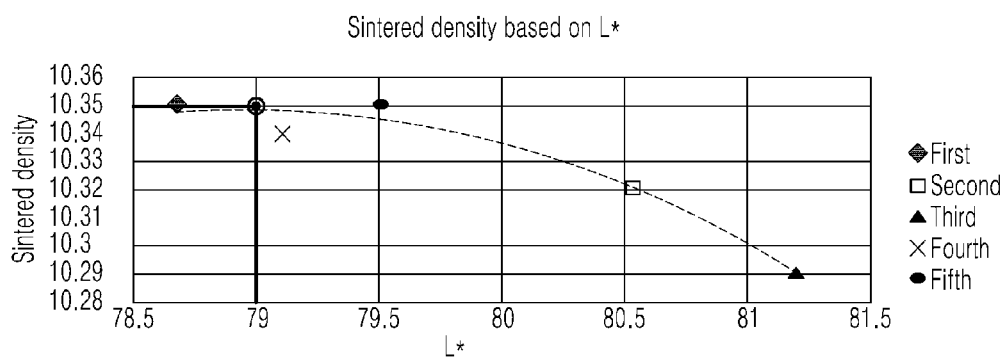
FIG. 6 is a graph showing the prediction of sintered density based on the relationship between the chromaticity value measured using the spectrophotometer and the sintered density.

The calculation of the sintered density using the L* value is shown in FIG. 6. Since the L* value is 79, the predicted value of the sintered density becomes 10.35, which was confirmed to be the same as the measured value after actual sintering.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of predicting a sintered density of a uranium oxide (UO$_x$) pellet for the nuclear fuel, the method comprising:
    obtaining standard data including a sintered density of a uranium oxide (UOx) pellet with respect to a chromaticity value of ammonium diuranate powder by measuring a sample uranium oxide (UOx) pellet and sample ammonium diuranate powder, wherein the sample ammonium diuranate powder is precursor of the sample uranium oxide (UOx) pellet;
    measuring a chromaticity value of target ammonium diuranate powder in a manufacturing process of a target uranium oxide (UOx) pellet using a spectrophotometer;
    finding a corresponding chromaticity value, in the standard data, to the chromaticity value of the target ammonium diuranate powder; and
    predicting the sintered density of the target uranium oxide (UO$_x$) pellet by obtaining the sintered density, from the standard data, with respect to the corresponding chromaticity value.

2. The method of claim 1, wherein the chromaticity values of the sample and target ammonium diuranate powders are obtained using a L* a* b* color coordinate system.

* * * * *